United States Patent [19]
Constantz

[11] Patent Number: 6,156,350
[45] Date of Patent: Dec. 5, 2000

[54] METHODS AND KITS FOR USE IN PREVENTING RESTENOSIS

[75] Inventor: Brent R. Constantz, Menlo Park, Calif.

[73] Assignee: Corazon Technologies, Inc., Menlo Park, Calif.

[21] Appl. No.: 09/454,235

[22] Filed: Dec. 2, 1999

[51] Int. Cl.$^7$ ..................................................... A61K 33/18
[52] U.S. Cl. ............................................................. 424/666
[58] Field of Search ............................................. 424/666

[56] References Cited

U.S. PATENT DOCUMENTS 5,902,610  5/1999  Hausheer et al. ........................ 424/649

OTHER PUBLICATIONS

Martindale The extra Pharmacopoeia 28th edition; p. 783, 1982.

Antoniucci, David, et al., "Current Role of Stenting in Acute Myocardial Infarction," *Am. Heart J.* (1999) vol. 138:S147–S152.

Casterella, Peter J., et al., "Prevention of Coronary Restenosis," *Cardiology in Review* (1999) vol. 7, No. (4):219–231.

Crocker, Ian, et al., "Radiation Therapy to Prevent Coronary Artery Restenosis," *Seminars in Radiation Oncology* (Apr. 1999) vol. 9, No. (2):134–143.

Gunn, J., et al., "Does Stent Design Influence Restenosis?," *European Heart Journal* (1999) vol. 20:1009–1013.

Johnson, G.J., et al., "The Utility of Animal Models in the Preclinical Study of Interventions to Prevent Human Coronary Artery Restenosis: Analysis and Recommendations," *Thromb Haemost* (1999) vol.:835–43.

Marso, Steven P., et al., "Intracoronary Stenting: An Overview for the Clinician," *Cleveland Clinic Journal of Medicine* (Jul./Aug. 1999) vol. 66, No. (7):434–442.

Rees, Chet R., "Stents for Atheroscerotic Renovascular Disease[1]," *JVIR* (1999) vol. 10, No. (6):689–705.

Thaulow, Erik, "Pharmacologic Effects of Calcium Channel Blockers on Restensosis," *Journal of Cardiovascular Pharmacology* (1999) vol. 33, (Suppl. 2):S12–S16.

Van Der Wieken, L.R., "Stents and llb/llla Receptor Blockers Combined: Usefulness in Various Types of Coronary Artery Disease," *Semin Intervent Cardiol* (1999) vol. 4:77–83.

Yutani, Chikao, et al., "Coronary Atheroscerosis and Interventions: Pathological Sequences and Restenosis," *Pathology International* (1999) vol. 49:273–290.

*Primary Examiner*—Raymond Henley, III
*Assistant Examiner*—Jennifer Kim
*Attorney, Agent, or Firm*—Bret Field; Bozicevic, Field & Francis

[57] ABSTRACT

Methods and kits are provided for at least inhibiting the progression of, if not preventing, restenosis in a host. In the subject methods, a vascular site is contacted, usually flushed, with a solution having a pH that is less than about 4, e.g. a hydrochloric acid. The subject methods find use in applications where the prevention of restenosis is desirable, including angioplasty applications, and may be used in combination with other treatment modalities, e.g. stents, and the like.

16 Claims, 5 Drawing Sheets

FIG. 5B

METHODS AND KITS FOR USE IN PREVENTING RESTENOSIS

TECHNICAL FIELD

The field of this invention is vascular disease, particularly restenosis and the prevention or treatment thereof.

BACKGROUND OF THE INVENTION

"Restenosis" refers to the renewed narrowing of an artery, e.g. a coronary artery, following a vessel opening or widening procedure, such as angioplasty or atherectomy. In restenosis, a vessel that has been treated to at least minimize the volume of a lesion or blockage and thereby restore blood flow, e.g. by balloon angioplasty, starts to renarrow, typically within about six months of the vessel widening procedure. This renarrowing often requires additional treatment, such as additional angioplasty procedures. It has been estimated that as much as one third to one half of all angioplasty procedures are followed by restenosis within the first six months to one year following the initial vessel widening procedure.

The cause of restenosis, and therefore identification of ways to prevent it, is the subject of intense interest. While it is known that restenosis is not caused by blood clots forming at the widened site, the cause of restenosis is not completely understood. One theory holds that restenosis is the cause of smooth muscle overgrowth of the vessel wall, perhaps as a result of the presence of large amounts of oxidants. Another theory holds that smooth muscle growth is not the primary cause of restenosis. Instead, restenosis results from scarring, which results in a remodeling and narrowing of the vessel.

A number of different protocols have been developed and/or are currently being investigated to treat and/or prevent restenosis. For example, antioxidant drugs such as probucol (Lorelco™) have been employed with some success. Other smooth muscle cell proliferation inhibitors that have been tested for their ability to inhibit restenosis include calcium channel blockers, e.g. verapamil, and proteins such as angiopeptin. Another potential technique for preventing restenosis that is currently being clinically evaluated involves the use of radiation, where the surface of the treated vessel is exposed to radiation, e.g. via the use of β-emitters. See e.g. the Beta-Cath™ System commercialized by Novoste Corporation and described at www.novoste.com. Yet other methods involve the use of stents to mechanically maintain the open vessel.

While a variety of different protocols are currently being tested for their effectiveness and safety in the prevention of restenosis (some of which have been described above), no particular technique has yet emerged as completely satisfactory. As such, there is continued interest in the development of new methods for preventing restenosis.

Relevant Literature van der Wieken LR, "Stents and IIb/IIIa receptor blockers combined: usefulness in various types of coronary artery disease," Semin Interv Cardiol (1999 June) 4(2):77–83; Antoniucci et al., "Current role of stenting in acute myocardial infarction," Am Heart J (1999 August) 138(2 Pt 2):147–52; Castella et al., "Prevention of Coronary Restenosis," Cardiol Rev (1999 July–August) 7(4):219–31; Marso et al., "Intracoronary stenting: an overview for the clinician," Cleve Clin J Med (1999 July–August) 66(7):434–42; Rees, "Stents for atherosclerotic renovascular disease," J Vasc Interv Radiol (1999 June) 10(6):689–705; Gunn et al., "Does stent design influence restenosis?" Eur Heart J (1999 July) 20(14):1009–13; Yutani et al., "Coronary atherosclerosis and interventions: pathological sequences and restenosis," Pathol Int (1999 April) 49(4):273–90; Johnson et al., "The utility of animal models in the preclinical study of interventions to prevent human coronary artery restenosis: analysis and recommendations. On behalf of the Subcommittee on Animal, Cellular and Molecular Models of Thrombosis and Haemostasis of the Scientific and Standardization Committee of the International Society on Thrombosis and Haemostasis," Thromb Haemost (1999 May) 81(5):835–43; Crocker, "Radiation therapy to prevent coronary artery restenosis," Semin Radiat Oncol (1999 April) 9(2):134–43; Thaulow, "Pharmacologic effects of calcium channel blockers on restenosis," J Cardiovasc Pharmacol (1999) 33 Suppl 2:S12–6.

SUMMARY OF THE INVENTION

Methods and kits are provided for at least inhibiting the progression of, if not preventing, restenosis in a host. In the subject methods, a vascular site is contacted, usually flushed, with a solution having a subphysiologic pH, e.g. an acidic solution such as a hydrochloric acid solution. The subject methods find use in applications where the prevention of restenosis is desirable and may be used in combination with other treatment modalities, e.g. stents, pharmacological restenosis inhibitors, and the like.

DESCRIPTION OF THE SPECIFIC EMBODIMENTS

Methods are provided for use in the prevention of restenosis. In the subject methods, a vascular site of a host is contacted, e.g. flushed, with a solution having a subphysiologic pH, e.g. a solution having a pH of less than about 4. The vascular site is contacted with the solution of reduced pH for a period of time sufficient for at least the progression of restenosis at the vascular site to at least be slowed, if not prevented. The subject methods may be used in conjunction with other restenosis prevention protocols, e.g. stenting. Also provided are kits for use in practicing the subject methods. In further describing the subject invention, the subject methods are reviewed first in greater detail, followed by a discussion of the subject kits and components thereof for practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Methods

As summarized above, the subject invention provides methods for at least slowing the progression of, if not preventing the occurrence of, restenosis at a vascular site of a host. In the subject methods, the target vascular site is contacted with a solution of subphysiologic pH for a period of time sufficient for the progression of restenosis at the target site to at least be slowed.

The target vascular site that is contacted with the solution of subphysiologic pH during the subject methods is one that has been previously treated for vascular occlusion, where the occlusion may be a partial or total occlusion. As such, the target vascular site is one that has the potential for restenosis, i.e. renarrowing of the vessel walls. The target vessel may be an artery or vein, and is usually an artery. The vascular site may be a peripheral or coronary vascular site, where the term peripheral is used broadly to refer to any site that is not a coronary vascular site. As such, peripheral vascular sites include not only limbic vascular sites but also core body vascular sites, e.g. carotid arteries, renal arteries, etc. In certain embodiments, the vascular site is a limbic peripheral vascular site, by which is meant that the vessel in which the vascular site is located is a vessel found in one of the extremities of the patient to be treated, i.e. the arms or legs. Often, the vascular site is a site in a lower extremity vessel, e.g. a lower extremity artery. As indicated above, of particular interest in certain embodiments are peripheral arterial vascular sites, where specific peripheral arteries of interest include: iliac arteries, femoropopliteal arteries, infrapopliteal arteries, femoral arteries, superficial femoral arteries, popliteal arteries, and the like. In yet other embodiments, the vascular site is present in a heart associated vessel, e.g. the aorta, a coronary artery or branch vessel thereof, etc. In yet other embodiments, the vascular site is present in a carotid artery or a branch vessel thereof.

The vascular site is characterized by having been treated for vessel narrowing or occlusion prior to practice of the subject methods. The vessel may have been treated for a total or partial occlusion, where the nature of the occlusion may vary greatly. Thus, the vessel may have been subject to an angioplasty or atherectomy procedure, where the initial vessel narrowing lesion has been manipulated in some fashion to enhance the blood flow rate through the vascular site. For example, the vascular site may be one that has been subjected to balloon angioplasty. Alternatively, the vascular site may be one that has been subjected to mechanical removal of at least a portion of the initially present lesion, e.g. through use of a device such as the Rotoblator™ device. In any event, the vascular site is one that is at least potentially subject to vessel renarrowing or reconstriction. In other words, the target vascular site is a site that has a propensity for vessel renarrowing, i.e. restenosis, to occur.

As mentioned above, the target vascular site is contacted with a solution of subphysiologic pH during practice of the subject methods. As the solution employed in the subject methods is a solution of subphysiologic pH, it is also properly referred to as an acidic solution. A variety of different types of acidic solutions may be employed in the subject methods. The acidic treatment solutions that find use in the subject methods generally have a pH of less than about 6.5, where the pH is usually less than about 4.0 and more usually less than about 3.0. In many preferred embodiments, the pH ranges from 0 to 2, and usually 0 to 1.

The acidic treatment solution can include a number of different types of acids, where the acids may or may not include a hydrocarbon moiety, i.e. a hydrogen bonded directly to a carbon atom. Suitable acids that lack a hydrocarbon moiety include halogen acids, oxy acids and mixtures thereof, where specific acids of interest of this type include, but are not limited to, hydrochloric, nitric, sulfuric, phosphoric, hydroboric, hydrobromic, carbonic and hydroiotic acids. For such acids, the acid can be a concentrated acid, or can be diluted. Upon dilution, the concentration of an inorganic acid will generally be from about 10 N to about 0.01 N, preferably between 5 N to 0.1 N. Also of interest are acids that include a hydrocarbon moiety, where such acids include, but are not limited to, any organic acid of one to six ($C_1$ to $C_6$) carbons in length. Organic acids of this type include, but are not limited to, formic, acetic, propionic, maleic, butanoic, valeric, hexanoic, phenolic, cyclopentanecarboxylic, benzoic, and the like. For an organic acid, the acid can be in concentrated form, or can be diluted. The acidic treatment solution can be composed of either a monobasic or a polybasic acid. Acids are "monobasic" when they have only one replaceable hydrogen atom and yield only one series of salts (e.g., HCl). Acids are "polybasic" when they contain two or more hydrogen atoms which may be neutralized by alkalies and replaced by organic radicals.

In many embodiments of the subject invention, the acid solution is hypertonic, by which is meant that the osmolarity of the solution is greater than that of whole blood, i.e. the osomolarity is greater than 300 mosmol. The solution may be rendered hypertonic by including any convenient component or components in the solution which provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Of particular interest in many embodiments is the use of a hydrogen chloride solution. In hydrogen chloride solutions that find use in the subject invention, the concentration of HCl in the solution ranges from about 0.001 to 1.0 N, usually from about 0.01 to 1.0 N and more usually from about 0.1 to 1.0 N. In many embodiments, the hydrogen chloride solution will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Of particular interest are aqueous hydrogen chloride solutions that consist of water, hydrogen chloride and NaCl. The concentration of hydrogen chloride in these solutions of particular interest ranges from about 0.01 to 1.0 N, usually from about 0.05 to 0.5 N and more usually from about 0.075 to 0.25 N. The concentration of NaCl in these solutions of particular interest ranges from about 0.05 to 0.25 M, usually from about 0.05 to 0.10 M.

In the subject methods, the vascular site, and specifically at least one wall and usually all of the walls of the target vascular site, is contacted with the acidic solution for a period of time sufficient for the progression of restenosis at the vascular site to be at least slowed, if not substantially or completely inhibited. Contact with the vascular site may be accomplished in any convenient manner, so long as it results in the enhancement of fluid flow through the vascular site.

The manner in which contact is achieved may be static or dynamic. By static is meant that a predetermined amount of acidic solution is introduced into the local environment of the vascular site and maintained in the local environment of the vascular site for the entire treatment period, without the addition of further quantities of acidic solution. By dynamic contact is meant that the fresh acidic solution is contacted with at least one surface of the target vascular site one or more times, including continuously, during the treatment period.

In certain embodiments of the subject methods, at least one surface of the target vascular site is continuously contacted or flushed with the acidic fluid. In other words, the acidic fluid is introduced in a manner such that a continuous flow of the acidic solution into the vascular site and walls thereof is achieved. Where the target vascular site is flushed with the dissolution fluid, it is preferred that the pressure in the local environment target vascular site, i.e. the area bounded by the vessel walls and the catheter system used to deliver the solution remains substantially isometric. By substantially isometric is meant that the pressure in the local environment does not vary by a significant amount, where the amount of variance over the treatment period does not vary by more than about 50%, usually by not more than about 10% and more usually by not more than about 5% In other words, the local environment remains substantially isobaric during the treatment period. Accordingly, where fluid is dynamically contacted with the surface of the target vascular site, fluid is also simultaneously removed from the local environment comprising the target vascular site, such that the overall volume of fluid in the local environment remains substantially constant, where any difference in volume at any two given times during the treatment period does not exceed about 50%, and usually does not exceed about 10%. As such, the dissolution fluid is introduced into the local environment of the target lesion in a manner such that the local environment remains substantially isovolumetric.

Where the acidic solution is dynamically introduced into and aspirated from the target vascular site, the fluid is introduced in a manner such that the flow rate of the dissolution solution through the vascular site of the lesion is generally at least about 10 cc/min, usually at least about 20 cc/min and more usually at least about 60 cc/min, where the flow rate may be as great as 120 cc/min or greater, but usually does not exceed about 1000 cc/minute and more usually does not exceed about 500 cc/minute, where by "volume" is meant the local environment of the target vascular site, as defined above. The total amount of dissolution fluid that is passed through the local environment of the target vascular site during the treatment period typically ranges from about 100 to 1000 cc, usually from about 200 to 800 cc and more usually from about 400 to 500 cc. The solution is generally pressurized to achieve the desired flow rate, as described supra. It is important to note that the overall pressure in the local environment is maintained at substantially isometric or isobaric conditions. As such, the negative pressure at the entrance to the aspiration catheter, e.g. the open annulus at the distal end of the aspiration catheter, will be of sufficient magnitude to provide for substantially isobaric conditions. Preferably, the overall pressure in the local environment is maintained at a value ranging from about 0.1 to 3 psi, usually from about 0.5 to 2.5 psi and more usually from about 1 to 2 psi.

The target vascular site is contacted, e.g. statically conctacted or flushed (as described above), with the acidic treatment fluid or solution for a period of time sufficient for the progression of restenosis in the target site to at least be slowed, if not substantially or completely inhibited. Generally, the period of time during which at least one surface of the target vascular site is contacted with the acidic solution ranges from about 1 to 100 minutes, usually from about 1 to 30 minutes, where in certain embodiments contact is from about 1 to 5 minutes, in other embodiments contact is from about 5 to 10 minutes and in yet other embodiments contact is from about 10 to 30 minutes. Where contact is achieved by flushing the target vascular with the acidic solution, the contact duration typically lasts for a period of time ranging from about 5 to 30 minutes, usually from about 10 to 30 minutes and more usually from about 10 to 20 minutes.

Any convenient fluid delivery device may be employed to contact the target vascular site with the acidic treatment solution, as described above. A large number of fluid delivery devices are known to those of skill in the art, where such devices include those described in U.S. Pat. Nos. 4,445,892; 4,573,966; 4,610,662; 4,636,195; 4,655,746; 4,824,436; 4,911,163; 5,059,178; 5,090,960; 5,163,905; 5,167,628; 5,176,638; 5,195,955; 5,222,941; 5,342,306; 5,380,284; 5,460,610; and 5,833,650; the disclosures of which are herein incorporated by reference. Of particular interest are those devices described in U.S. patent application Ser. Nos. 09/118,193; 09/195,291; 09/353,127; PCT/US99/15918; 09/382,571; and 09/384,860; the disclosures of which are herein incorporated by reference.

The subject methods result in at least a slowing of, if not a substantial or complete inhibition of, restenosis in the treated target vascular site. By "slowing of the progression of" is meant that the rate of vessel narrowing at a treated vascular site is slower than the rate of vessel narrowing in a control site, e.g. a vascular site which is not contacted with an acidic solution according to the subject methods. The progression of restenosis is considered to be at least slowed if the rate of vessel narrowing is at least about 5%, usually at least about 10% and more usually at least about 15% slower than vessel narrowing in a control target vascular site. In certain embodiments, the rate of vessel narrowing in the treated vascular site is at least 50%, usually at least 60% and more usually at least 75% slower than the rate observed in control target vascular sites. In yet other embodiments, restenosis is substantially, if not completely inhibited in the treated target vascular site, by which is meant that there is substantially no, if any, vessel renarrowing in the treated site, at least for a substantial period of time, e.g. for at least about 1 year, usually for at least about 2 years.

The subject methods find use in a variety of different applications in which it is desired to at least slow the progression of, if not substantially or completely inhibit the appearance of, restenosis or renarrowing of a vessel. As such, the subject methods find use in conjunction with a wide variety of vessel widening procedures. Representative vessel widening procedures with which the subject methods may be employed include: angioplasty, atherectomy, stenting, stent grafting, and the like, wherein such procedures are described and reviewed at, among other places, the internet web site of the American Heart Association, which site has an address of http://www.americanheart.org.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

Kits

Also provided by the subject invention are kits for use in a least slowing the progression of, if not substantially or completely inhibiting the appearance of, restenosis in a target vascular site. The subject kits at least include: an acidic solution or precursors thereof and a fluid delivery means for delivering the acid solution to the target vascular site. The solution or one or more precursors thereof may be present in a container(s), e.g. a flexible bag, a rigid bottle, etc. For kits that are to be used in methodologies in which the fluid is flushed through the local environment of the target vascular site, the amount of acidic fluid present in the kit ranges from about 0.5 to 500 liters, usually from about 0.5 to 200 liters and more usually from about 0.5 to 100 liters. In many of these embodiments, the amount of acidic fluid in the kit ranges from 0.5 to 5 liters, usually from about 0.5 to 2.0 liters and more usually from about 0.5 to 1.5 liters. In contrast, where the fluid is to be contacted statically with the vascular site, the kit may include much less dissolution fluid. In these embodiments, the amount of dissolution fluid that may be present in the kit may range from about 0.5 ml to 100 ml, usually from about 5 ml to about 50 or 20 ml, and more usually from about 5 to 15 ml. As mentioned above, the kit may alternatively include precursors of the dissolution solution for use in preparing the solution at the time of use. For example, the precursors may be provided in dry form for mixing with a fluid, e.g. water, at the time of use. The kits also include a fluid delivery means for delivering the acidic fluid to the target vascular site. Generally, the kits include a catheter device or system, where representative catheter devices and systems are described in supra. The kits may further include one or more additional components and accessories for use with the subject catheter systems, including tubing for connecting the various catheter components with fluid reservoirs, syringes, pumping means, etc., connectors, one or more guidewires, dilators, vacuum regulators, etc. Finally, the kits include instructions for practicing the subject methods, where such instructions may be present on one or more of the kit components, the kit packaging and/or a kit package insert.

The following examples are offered by way of illustration and not by way of limitation.

EXPERIMENTAL

I. Rabbit Assay

The following protocol was used to test various solutions for their effect on smooth muscle cell proliferation in arterial walls following angioplasty. A segment of the abdominal aorta of a New Zealand White rabbit (>4 kg) is rendered bloodless by inserting catheters both proximally and distally to the region, inflating balloons at the distal tip of each catheter to occlude blood flow and isolating the segment, and flushing the segment with heparinized buffer. Next, a test solution is circulated through the region (various test solutions are described below), followed by flushing and deflation of the balloons.

Figure 1A:
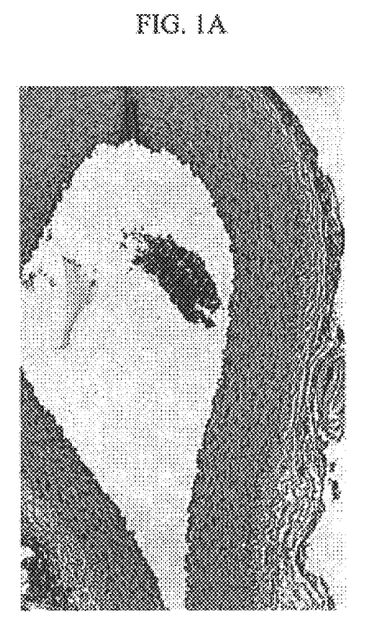
FIGS. 1A and 1B show a normal untreated aorta at both 25× and 100× magnification.
Figure 1B:
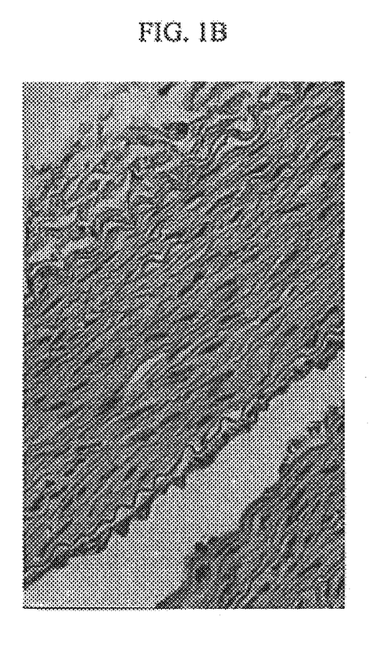
Figure 2A:
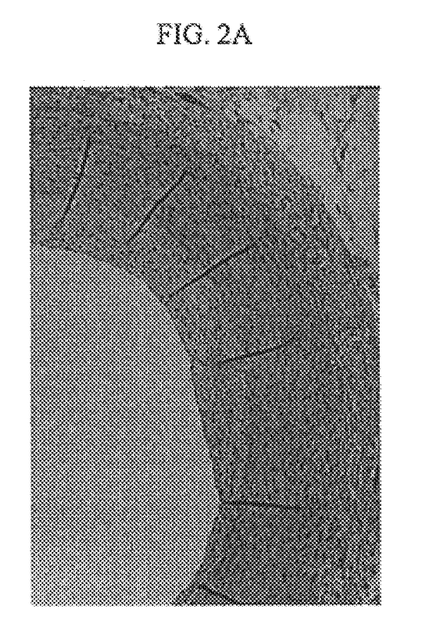
FIGS. 2A and 2B show an aorta that was ballooned and treated with a control saline solution at 2 weeks.
Figure 2B:
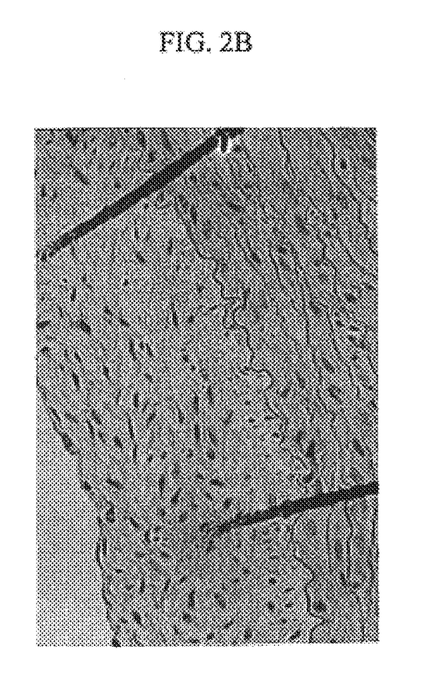
Figure 3A:
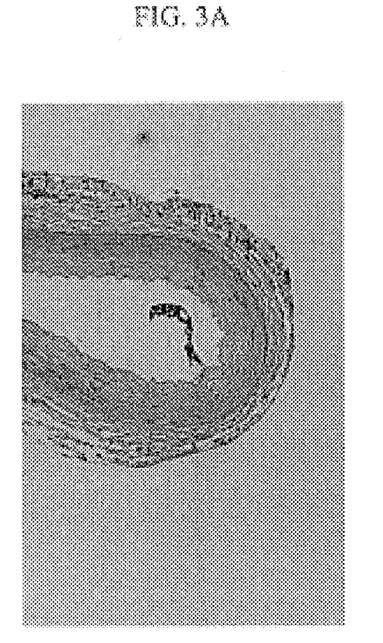
FIGS. 3A and 3B show an aorta (at 25× and 100× magnification, respectively) that was ballooned and then treated with test solution A.
Figure 3B:
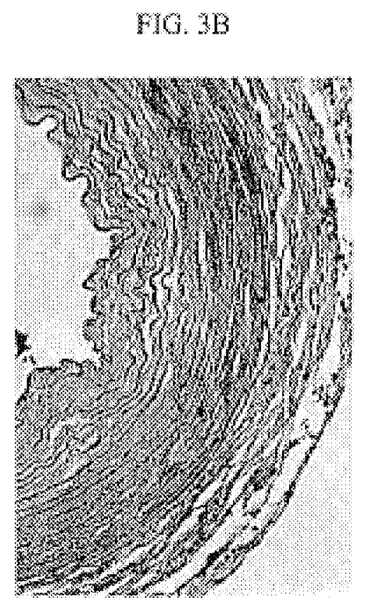
Figure 4A:
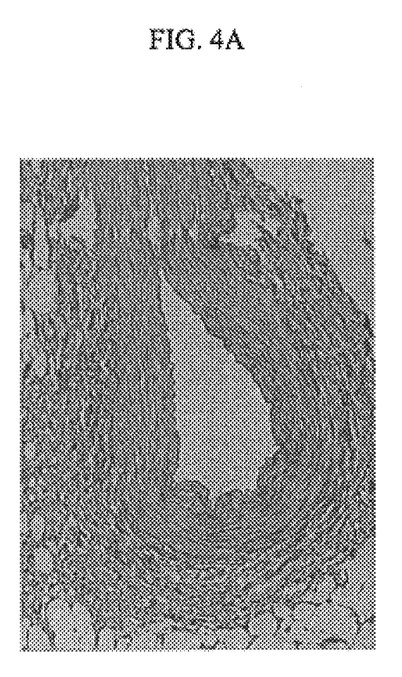
FIGS. 4A and 4B aorta (at 25 and 100× magnification, respectively) show the histology of an aorta that was ballooned and then treated with test solution B.
Figure 4B:
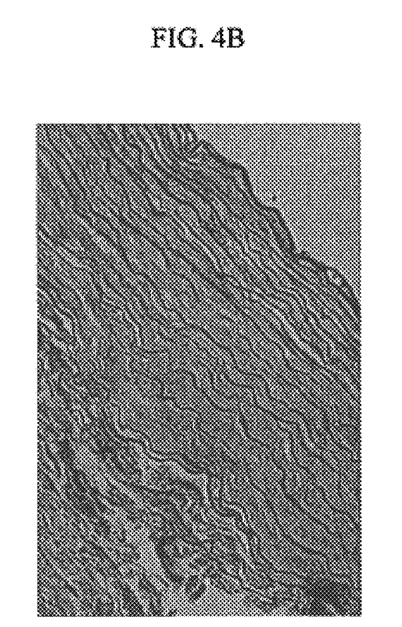
Figure 5A:
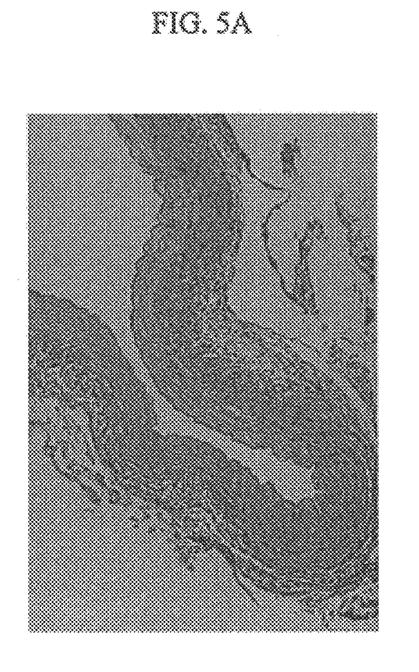
FIGS. 5A and 5B show an aorta (at 25 and 100× magnification, respectively) that was ballooned and treated with a control saline solution at 3 days.
Figure 5B:
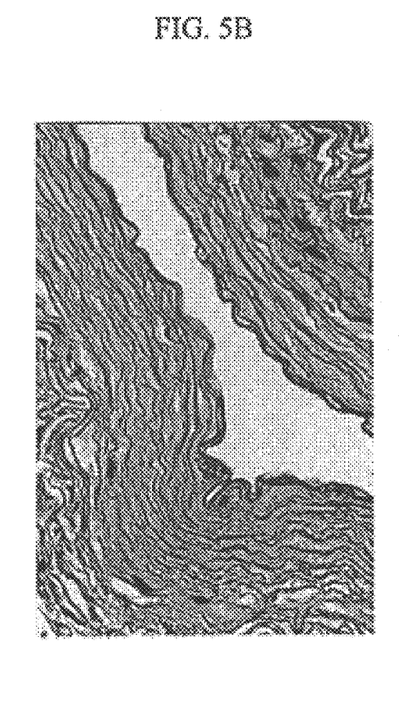

The response of the treated segments to various test solutions over time was characterized histologically. FIGS. 1A and 1B show a normal untreated aorta at both 25× and 100× magnification. FIGS. 2A and 2B show an aorta that was ballooned and treated with a control saline solution at 2 weeks. In the figures, the superpositional zone on the left is neointimal hyperplasia infilling the lumen. FIG. 2A is 25× and FIG. 2B is 100× magnification. FIGS. 3A and 3B show an aorta (at 25× and 100× magnification, respectively) that was ballooned and then treated with a 1 N HCl solution adjusted with sufficient NaCl to have an osmotic pressure of 300 mosmols. FIGS. 4A and 4B (at 25× and 100× magnification, respectively) show the histology of an aorta that was ballooned and then treated with a 0.1 N HCl solution adjusted with sufficient NaCl to have an osmotic pressure of 300 mosmols. FIGS. 5A and 5B show an aorta (at 25× and 100× magnification, respectively) that was ballooned and treated with a control saline solution at 3 days. The absence of cell nuclei in the medial layer indicates cell necrosis, likely due to the crushing mechanical injury during the balloon inflation.

The above results demonstrated that treatment of a ballooned aorta with an acidic solution inhibits subsequent smooth muscle growth and therefore is effective in preventing restenosis.

II. A 50 year old male having a coronary artery occlusion is treated using balloon angioplasty according to standard surgical protocols. Balloon angioplasty results vessel widening by compressing the plaque initial present in the target vessel site against the walls of the vessel. Following balloon angioplasty, the fluid delivery device described in U.S. patent application Ser. No. 09/384,680 is used to flush the treated vascular site with an acidic solution according to the protocol provided below. An introducer sheath is placed in a suitable location and a guidewire is inserted and advanced to the target vascular site. The catheter system described in U.S. patent application Ser. No. 09/384,680 is employed as follows. The partial occlusion catheter device is inserted so that the distal end of the device is at a position such that the balloon at the distal end of the insert is on the far side of the target vascular site. A system as shown in FIG. 5B of the referenced application is then employed to inflate the balloon of the insert, establish a bloodless local environment and flush the target vascular site with acidic fluid. Following treatment, the progression of restenosis in the treated site is at least slowed.

It is evident from the above discussion and results that improved methods of treating restenosis are provided. Specifically, the subject methods provide for a simple, safe and effective means for at least slowing the progression of, if not preventing, restenosis. The subject methods are simple in that readily manufactured and safe acidic solutions are employed. The subject methods are also safe, in that relatively non-toxic agents are locally administered. Despite their safety and simplicity, the subject methods provide an effective method for at least reducing the progression of restenosis. As such, the subject invention represents a significant contribution to the field.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. In a method of treating a vascular disease condition, the improvement comprising:

contacting a vascular site of a host suffering from said condition with a solution having a subphysiologic pH.

2. The method according to claim 1, wherein said contacting is by flushing.

3. The method according to claim 1, wherein said solution is an inorganic acid solution.

4. The method according to claim 3, wherein said inorganic acid solution is a hydrochloric acid solution.

5. The method according to claim 1, wherein said disease condition is restenosis.

6. A method for at least slowing the progression of restenosis at a vascular site of a host, said method comprising:

contacting said vascular site of a host with a solution having a subphysiologic pH.

7. The method according to claim 6, wherein said vascular site is statically contacted with said solution.

8. The method according to claim 6, wherein said vascular site is flushed with said solution.

9. The method according to claim 6, wherein said solution is an inorganic acid solution.

10. The method according to claim 9, wherein said inorganic acid solution is a hydrochloric acid solution.

11. A method for at least slowing the progression of restenosis at a vascular site of a patient, said method comprising:

contacting said vascular site with a hydrochloric acid solution having a pH of less than about 4.

12. The method according to claim 11, wherein said vascular site is statically contacted with said hydrochloric acid solution.

13. The method according to claim 11, wherein said vascular site is flushed with said hydrochloric acid solution.

14. The method according to claim 11, wherein said hydrochloric acid solution has a pH that does not exceed about 2.

15. The method according to claim 11, wherein said hydrochloric acid solution further includes a salt.

16. The method according to claim 15, wherein said salt is NaCl.

* * * * *